United States Patent
Lenner et al.

(10) Patent No.: US 10,281,315 B2
(45) Date of Patent: *May 7, 2019

(54) SYSTEM AND METHOD FOR MEASURING A SPEED OF SOUND IN A LIQUID OR GASEOUS MEDIUM

(71) Applicant: ABB Schweiz AG, Zürich (CH)

(72) Inventors: Miklos Lenner, Baden-Dättwil (CH); Tobias Kaufmann, Zürich (CH); Detlef Pape, Nussbaumen (CH)

(73) Assignee: ABB Schweiz AG, Baden (CH)

( * ) Notice: Subject to any disclaimer, the term of this patent is extended or adjusted under 35 U.S.C. 154(b) by 112 days.

This patent is subject to a terminal disclaimer.

(21) Appl. No.: 15/202,146

(22) Filed: Jul. 5, 2016

(65) Prior Publication Data
US 2017/0010144 A1    Jan. 12, 2017

(30) Foreign Application Priority Data

Jul. 6, 2015 (EP) ..................................... 15002013
Nov. 25, 2015 (EP) ..................................... 15196208

(51) Int. Cl.
*G01F 23/296* (2006.01)
*G01H 5/00* (2006.01)
(Continued)

(52) U.S. Cl.
CPC ...... *G01F 23/2962* (2013.01); *G01F 23/2968* (2013.01); *G01H 5/00* (2013.01);
(Continued)

(58) Field of Classification Search
CPC .................................................. G01F 23/2962
(Continued)

(56) References Cited

U.S. PATENT DOCUMENTS 3,277,433 A * 10/1966 Toulis ................... B06B 1/0618
                                                310/337
4,954,997 A *  9/1990 Dieulesaint ......... G01F 23/2961
                                                340/621
(Continued)

FOREIGN PATENT DOCUMENTS

| DE | 68903015 T2 | 5/1993 | |
| DE | 19900832 A1 | 7/2000 | |
| JP | 2006322825 A * | 11/2006 | ............. G01F 23/28 |
| RU | 2112221 C1 | 5/1998 | |
| WO | 2010034713 A2 | 4/2010 | |

OTHER PUBLICATIONS

European Search Report dated Jul. 12, 2016; European Application No. 15196208.1; ABB Schweiz AG; 9 pgs.

*Primary Examiner* — John Fitzgerald
*Assistant Examiner* — Jean Morello
(74) *Attorney, Agent, or Firm* — Taft Stettinius & Hollister LLP; J. Bruce Schelkopf

(57) ABSTRACT

A system and a method for measuring a speed of sound in a liquid contained in a vessel or in a gaseous medium contained in the same vessel above the surface of the liquid. The method comprises: transmitting a first acoustic signal into the vessel to travel inside a first travelling plane. Emitting a second acoustic signal into the wall of the vessel to travel inside the wall of the vessel along a perimeter of the first travelling plane until it is received and obtaining a first time of flight of the first acoustic signal and a second time of flight of the second acoustic signal and obtaining a speed of sound in the vessel wall from a data memory. Determining the speed of sound in the liquid or in the gaseous medium from the length of the travelling path of the first acoustic signal and from the first time of flight.

20 Claims, 4 Drawing Sheets

Figure 2:
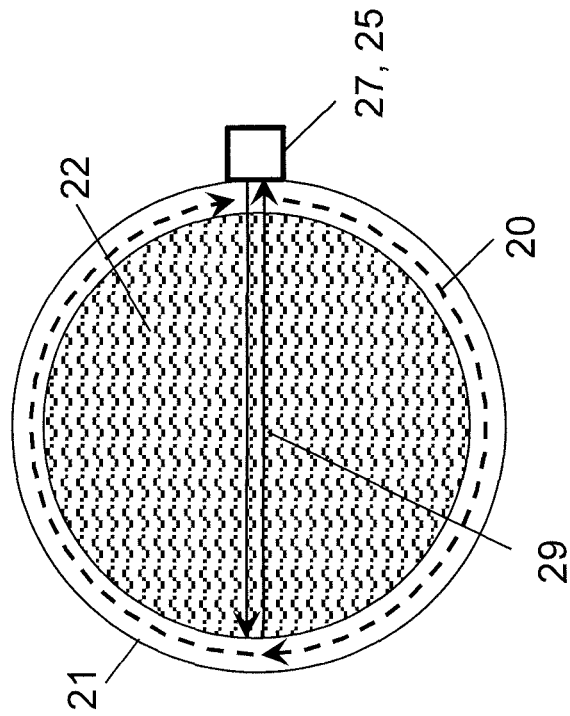

(51) Int. Cl.
*G01N 29/024* (2006.01)
*G01S 7/52* (2006.01)
*G01S 7/539* (2006.01)
*G01S 15/87* (2006.01)
*G01S 15/88* (2006.01)
*G01S 15/10* (2006.01)

(52) U.S. Cl.
CPC ........ *G01N 29/024* (2013.01); *G01S 7/52006* (2013.01); *G01S 7/539* (2013.01); *G01S 15/878* (2013.01); *G01S 15/88* (2013.01); *G01N 2291/011* (2013.01); *G01N 2291/02836* (2013.01); *G01S 15/10* (2013.01)

(58) Field of Classification Search
USPC ........................................................ 73/290 V
See application file for complete search history.

(56) References Cited

U.S. PATENT DOCUMENTS

| | | | |
|---|---|---|---|
| 5,251,487 A | 10/1993 | Marshall | |
| 6,053,041 A * | 4/2000 | Sinha | G01F 23/28 340/621 |
| 6,925,870 B2 | 8/2005 | Pappas et al. | |
| 7,694,560 B1 | 4/2010 | Dam et al. | |
| 8,661,904 B2 * | 3/2014 | Schmitt | G01B 17/025 73/290 V |
| 2005/0072226 A1 | 4/2005 | Pappas et al. | |
| 2011/0132090 A1 * | 6/2011 | Sohn | G01N 29/041 73/599 |
| 2016/0209539 A1 * | 7/2016 | Le Calvez | E21B 47/0005 |
| 2017/0010146 A1 * | 1/2017 | Kassubek | G01N 29/222 |

* cited by examiner

SYSTEM AND METHOD FOR MEASURING A SPEED OF SOUND IN A LIQUID OR GASEOUS MEDIUM

The invention relates to a system and a method for measuring a speed of sound in a liquid contained in a vessel, or in a gaseous medium contained in the same vessel above the surface of the liquid.

To know the speed of sound in a liquid or in a gaseous medium, i.e. to know the propagation speed of an acoustic wave travelling through the medium, is an important prerequisite when continuously determining the filling level of a liquid in a vessel.

For continuously determining the filling level, continuous level sensors are used. Today, continuous level measurement methods mainly use an intrusive technique which means that an opening in the wall of the vessel is needed to introduce the level sensor into the vessel. The intrusive techniques may be based on acoustic or on electromagnetic, in particular radar, signals which are sent towards the liquid surface where they are reflected back.

However, in certain industries, such as in the food or pharmaceutical industry, it is undesirable to bring a foreign object into close proximity of or even contact with the liquid, in order to avoid contamination. In even other areas, such as in the chemical or in the oil and gas industry, intrusive level measurement may not be indicated due to the liquids being explosive, easily inflammable, corrosive or being subject to extreme temperatures. For these conditions, non-intrusive continuous level measurement techniques are used which are based on measuring the filling level of a closed vessel.

The majority of intrusive and the non-intrusive continuous level measurement methods are based on the time of flight measurement of an acoustic or electromagnetic pulse, where the travel time of a signal towards the interface between liquid and a gas filling the space above the liquid, as well as its reflection at the interface backwards to the receiver are measured. The level height can then be determined out of the measured time and the sound velocity of the medium in which the signal propagates.

In particular, either a pulse is sent from the bottom of a tank or vessel through the liquid and upwards towards the interface between liquid and gas, as in U.S. Pat. No. 7,694,560B1; or the pulse is sent in the opposite direction from the inner top of the vessel through the gas to the interface. This interface may also be called liquid surface or level interface. From the level interface, the pulse is reflected back, and received again at a certain location. The propagation distance L and thus the filling level can then be calculated by dividing the propagation time t of the pulse by the propagation velocity c, under the assumption that the propagation velocity c is known.

Figure 1:
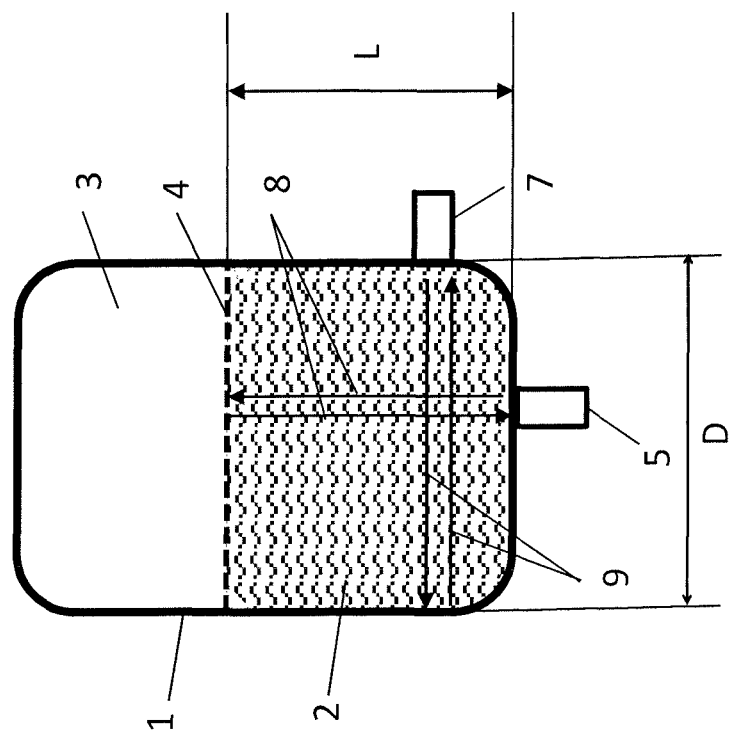

In JP2006322825A, a non-intrusive liquid level measuring method is described which applies above described level measuring technique. The general setup is shown in FIG. 1. Here, a vessel 1 contains a liquid 2 and a gaseous medium 3 above the liquid 4. The interface between the liquid 2 and the gaseous medium 3 is called liquid surface 4 or level interface. The time of flight of an ultrasonic pulse 8 is measured, where the ultrasonic pulse 8 is transmitted from the outside of the bottom of the vessel 1 by a first ultrasonic transmitter-receiver 5 and reflected back by the liquid surface 4. In order to calculate the filling level of liquid 2, the propagation velocity of the ultrasonic wave, i.e. its speed of sound in the liquid 2, is needed. The speed of sound is determined by a second ultrasonic transmitter-receiver 7 which is positioned at a side wall of the tank and which measures the time of flight of a second pulse 9 along the horizontal diameter of the vessel 1. It is required in JP2006322825A that the diameter of the vessel 1 is a known magnitude, so that the speed of sound of the ultrasonic pulse 9 is calculated directly.

In other words, in FIG. 1, an acoustic signal 8 is sent towards the level interface or liquid surface 4, where it is reflected back and then received by the same transducer 5. The time of flight t of the acoustic signal 8 is measured. The distance L from the transducer 5 to the liquid surface 4, and thereby the liquid level, is then calculated by multiplying the propagation speed c_medium of the signal in the liquid 2, which is for acoustical signals the speed of sound, with half the time of flight t, i.e.

$$L=(t*c\_medium)/2 \quad (1).$$

From U.S. Pat. No. 6,925,870B2, another non-intrusive ultrasonic level sensor is known where a transmitter-receiver of an acoustic signal is located at a side wall of the vessel. Again, a first ultrasonic signal is emitted in horizontal direction and reflected back from the opposite side wall of the vessel. This signal is used for measuring the speed of sound, i.e. the travel speed of the ultrasonic beam, in the liquid. A second ultrasonic signal is emitted in an angular direction in such a way that it is reflected back by the intersection between the liquid surface and the opposite side wall of the vessel. From the previously determined speed of sound and from the time of flight of this second signal, the length of its inclined path is obtained. The height of the liquid surface relative to the location of the transducer is then calculated as the altitude of a right triangle having hypotenuse and leg corresponding to the lengths of the first and second ultrasonic travelling paths. Also in U.S. Pat. No. 6,925,870B2 it is presumed that the distance traveled by the horizontal signal is known beforehand in order to directly calculate the speed of sound.

In contrast to continuous level sensors as described above, there exist so called point level sensors which only detect whether a predefined level is exceeded by a liquid surface or not. Point level sensors are for example described in DE19900832A1, where the reflectivity change for a sound pulse at the wall/medium interface is used as an indicator for the present, of liquid, or in DE68903015T2, RU2112221C1 and Sakharov et.al., "Liquid level sensor using ultrasonic Lamb waves", Ultrasonics 41 (2003), pp. 319-322. The technology described in the latter is based on the use of ultrasonic Lamb waves propagating along the vessel wall or walls.

Lamb waves or also called plate waves are mechanical waves generated in plates where the wave propagation is influenced by the reflection of the wave at the sides of the walls and the thus limited propagation space, They thus show similar properties as waves propagating in wave guides. Lamb waves are propagating in different modes with different properties, in particular different propagation velocities as well as different attenuations. Typically at low frequencies, a symmetric S0 and an antisymmetric A0 mode can occur. Ideally, the waves are reflected totally at the sides of the plate and are thus kept inside the plate. This is valid in a first approximation for plates in a gaseous medium or in vacuum.

In the case of a contact of the plate with a liquid, the reflectivity of the interface is reduced and the Lamb waves can emit acoustic energy into the surrounding liquid medium. This occurs especially for the asymmetric mode at low frequencies. Due to the emitting of acoustic energy into the surrounding medium, they are also called leaky Lamb waves. This emitting of acoustic energy into the liquid results in a strong attenuation of the wave, which effect is especially used in the point level sensors of DE68903015T2, RU2112221C1 and Sakharov for the detection of the presence of liquid.

The basic principle behind the Lamb wave sensors is thus the fact that a contact between the vessel wall and the liquid substantially attenuates the Lamb wave, which effect is used as an indicator of liquid presence. While the point level sensors of DE68903015T2 and Sakharov are purely based on Lamb waves travelling inside the vessel walls, the point level sensor of RU2112221C1 emits both a Lamb wave into the vessel wall and a longitudinal ultrasound wave into the liquid. Both waves propagate horizontally and in parallel to the liquid surface. By measuring the attenuation, i.e. the damping of the amplitude, of the two signals, a more reliable and accurate result is obtained.

It is to be noted that point level sensors using Lamb waves as well as sensors described in DE19900832A1 are based on an amplitude measurement of the sound signals and do not measure any time of flight. They therefore need not to determine any speed of sound. They can detect the presence of liquid in the proximity of the sensor at a distance of a few centimeters or decimeters but are not suited to continuously measure the level over longer distances.

Coming back to continuous level sensors, it can be noted that in general the determination of the speed of sound is a critical point for acoustic level measurements, and that the speed of sound has to be known in advance. However, the speed of sound depends on the medium and varies with the temperature.

The speed of sound varies for example for gases from 130 m/s for SF6 to 1260 m/s for hydrogen (H2), which is a variation of approximately 950%. For common gases, the variation in the speed of sound is about 70%, between the 250 m/s for carbondioxide (CO2) and 430 m/s for methane (CH4). For gases, the temperature variation is about 1800 ppm/K at room temperature.

In liquids, the speed of sound may vary from 943 m/s for carbon tretrachloride (C Cl4) to 1660 m/s for aniline, which corresponds to a variation of about 70%. In water, the temperature variation is again about 1800 ppm/K at room temperature.

In those metals which are commonly used as a material for vessel walls, the speed of sound varies depending on whether the acoustic signal inside the wall is a longitudinal wave or a shear wave. For longitudinal waves, the speed of sound in steel is 5400 m/s, in aluminum 5100 m/s and in Invar, which is a Ni/Fe alloy, 4300 m/s. This corresponds to a variation of 25%. For shear waves, the speed of sound in steel is 3200 m/s, in aluminum 3100 m/s and in Invar 2700 m/s, which corresponds to a variation of 18%. The temperature variation in wall metals is 150 ppm/K.

Accordingly, it can be observed that a considerable change may occur in the speed of sound of a liquid or a gaseous medium, so that the speed of sound needs to be individually determined before measuring the level of a liquid in a vessel.

In an application, where mainly air is expected as propagation medium, and where no high accuracy requirements are needed, simple correlations together with temperature measurements are used to determine the speed of sound for the level calculation. In order to obtain a higher precision, an additional time of flight measurement of a signal reflected over a known distance D is used to determine the speed of sound by using equation (1) in reverse mode.

$$c\_medium = (2*D)/t \qquad (2).$$

In intrusive level measurement devices which are mounted inside the vessel, this fixed distance can be integrated into the sensor and is thus well known. For known non-intrusive devices, the width of the vessel is taken as a fixed distance D for the speed of sound measurement, as shown in FIG. 1. This distance D has then to be measured during the installation of the device and to be entered by the user in order to be saved in a data memory for later use during the level measurement.

The measurement of the distance D can be difficult depending on the shape of the tank or vessel and the size of the tank. Especially for very big tanks, this can be quite challenging. Therefore, the determined distance D can be relatively imprecise which will directly affect the accuracy of the overall level measurement. Additionally, the manual entering of the distance D is prone to errors. The exact determination of this fixed distance D is therefore a very critical point for the determination of the speed of sound, and it will directly influence the performance and accuracy of the whole level measurement system.

Therefore, it is an object of the present invention to provide an alternative system and an alternative method for measuring the speed of sound in a liquid or in a gaseous medium which no longer requires that the travel length is known beforehand.

This object is achieved by a system and a method according to the independent claims.

As is known from the above described art, a first acoustic transmitter is mounted on one side of the liquid surface for transmitting a first acoustic signal into the liquid or into the gaseous medium to travel inside a first travelling plane. The phrase "on one side" means hereby that the transducer is placed in a horizontal plane which lies either above or below the liquid surface, and the transducer may be mounted at the outside or at the inside of the vessel containing the liquid and the gaseous medium.

A first acoustic receiver is mounted on the same side of the liquid surface as the first transmitter for receiving the first acoustic signal. Accordingly, the receiver is placed in a horizontal plane which is above the liquid surface if the transducer is above the liquid surface or below the liquid surface if the transducer is below the liquid surface. The horizontal planes of the transducer and of the receiver do not necessarily have to be the same, i.e. they can differ in their vertical positions.

At least one electronic control and data processing unit is provided for controlling operation of the transmitter and of the receiver and for determining the speed of sound from a time of flight of the first acoustic signal.

According to the invention, the first transmitter or a second transmitter is further arranged to emit a second acoustic signal in form of an acoustic wave into the wall of the vessel to travel inside the wall of the vessel along a perimeter of the first travelling plane until it is received by the first acoustic receiver or by a second acoustic receiver which is placed at a predetermined distance from the first or second transmitter, respectively.

The at least one electronic control and data processing unit is arranged to
    obtain a first time of flight of the first acoustic signal and a second time of flight of the second acoustic signal by measuring the period of time between emission and reception of the respective signal;
    obtain a speed of sound in the vessel wall from a data memory;

determine the perimeter of the first travelling plane from the speed of sound in the vessel wall and from the second time of flight, determine the length of the travelling path of the first acoustic signal from the perimeter of the first travelling plane and from an information on the geometric shape of the first travelling plane, determine the speed of sound in the liquid or in the gaseous medium from the length of the travelling path of the first acoustic signal and from the first time of flight.

From the above, it can be understood that the term "time of flight" relates to the time which elapses between emission and reception of a signal.

Further, it is to be noted that the at least one electronic control and data processing unit of the proposed system is adapted to perform all the steps described in the following for obtaining the measurements and for determining the various magnitudes which it then uses for generating, as an output result, the speed of sound in the liquid or in the gaseous medium. The speed of sound in the liquid or in the gaseous medium may then be transmitted to a level measurement device, or it may be used by the at least one electronic control and data processing unit itself during measurement of the liquid level in the vessel.

Due to the invention, a speed of sound calibration is provided to be used in connection with non-intrusive level measurements, so that a level measurement can be performed without the user needing to measure the required geometric dimension of the vessel in advance.

The proposed solution is based on the recognition of the fact that the speed of sound in a solid wall varies much less with the wall material and the temperature than the speed of sound in the liquid or gaseous medium in the vessel. Accordingly, the speed of sound in the vessel wall can be assumed to be known.

The solution described here may advantageously be applied in a non-intrusive level measurement device, which as a result can automatically self-determine the necessary dimensions and parameters required for the calibration of the sound velocity and consequently for the level measurement. Since the level measurement no longer relies on predetermined magnitudes, the reliability and the accuracy of the level measurement will be increased.

Figure 4:
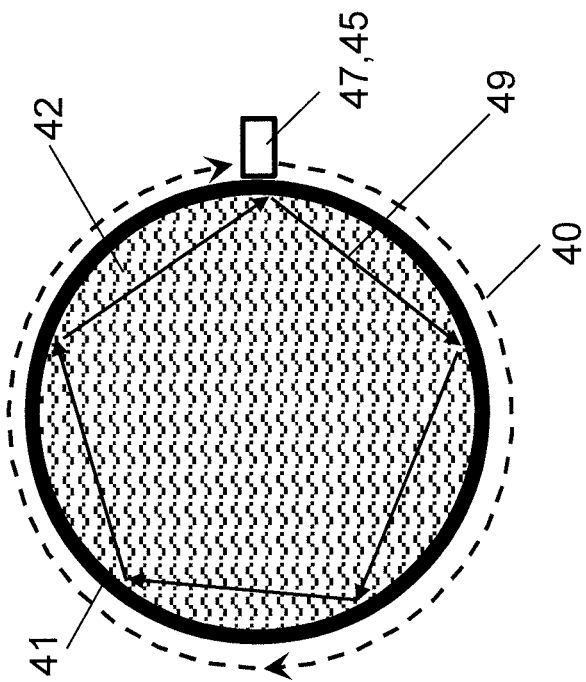
Figure 3:
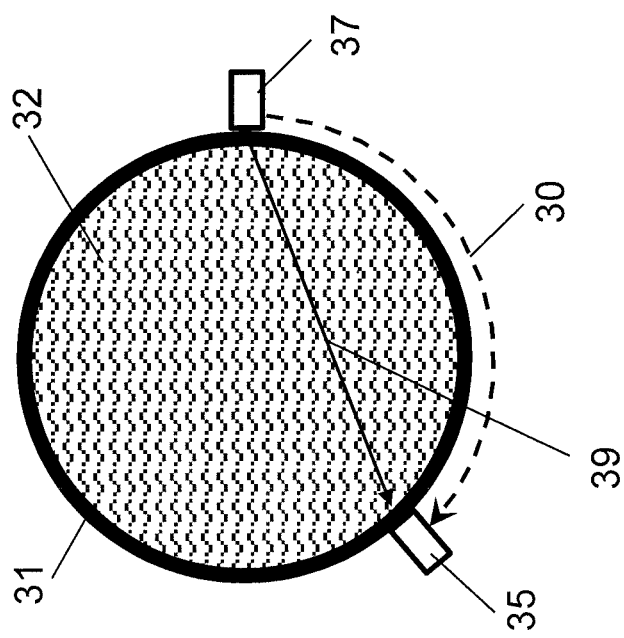

Based on the above described general idea, different embodiments are suggested which are discussed in the following in connection with the examples shown in the appended drawings. The drawings illustrate:

FIG. 1 a side view of a set-up for level measurement in a vessel as previously known, including the measurement of the speed of sound in a liquid;

FIG. 2 a first embodiment for measuring the speed of sound in the liquid;

FIG. 3 a second embodiment for measuring the speed of sound in the liquid;

FIG. 4 a third embodiment for measuring the speed of sound in the liquid; and

Figure 5:
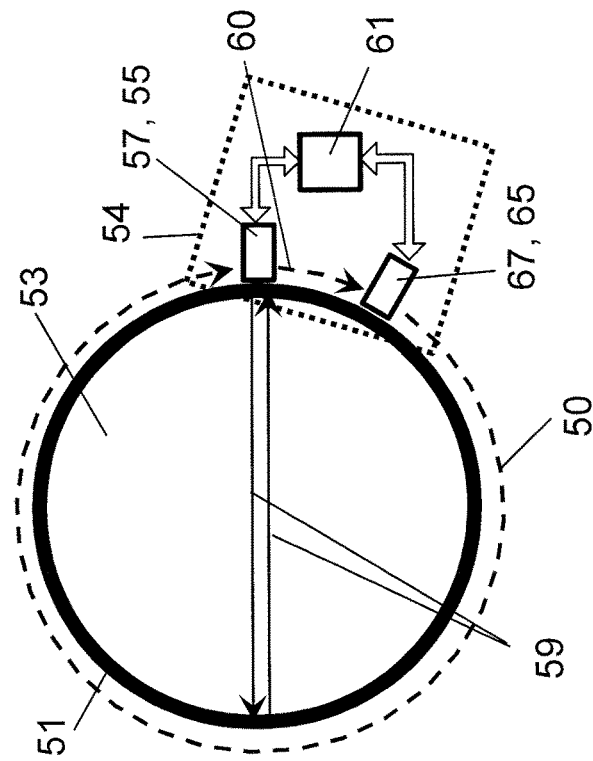
Figure 6:
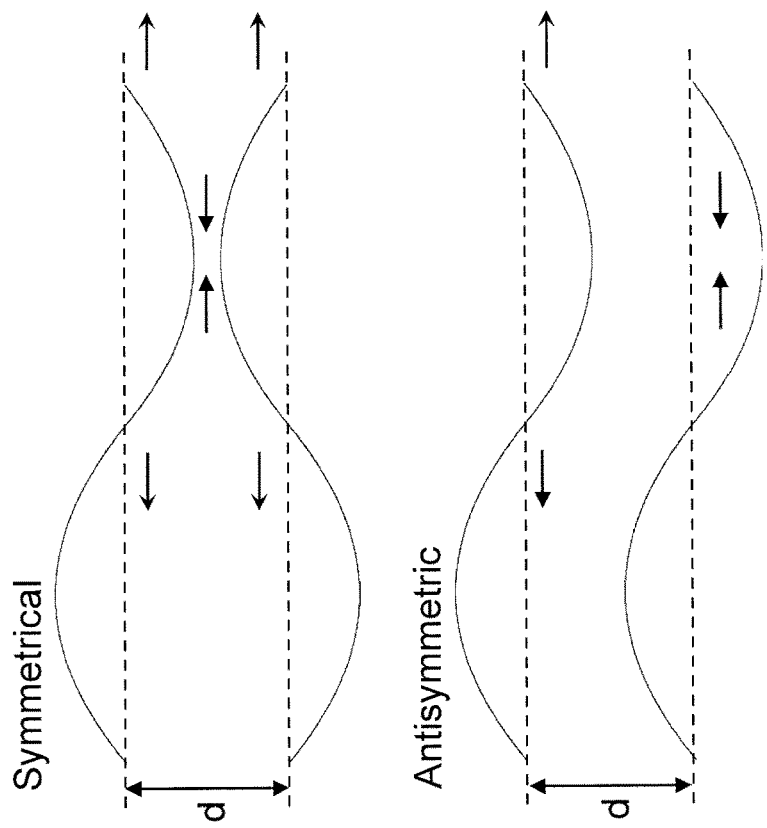
Figure 7:
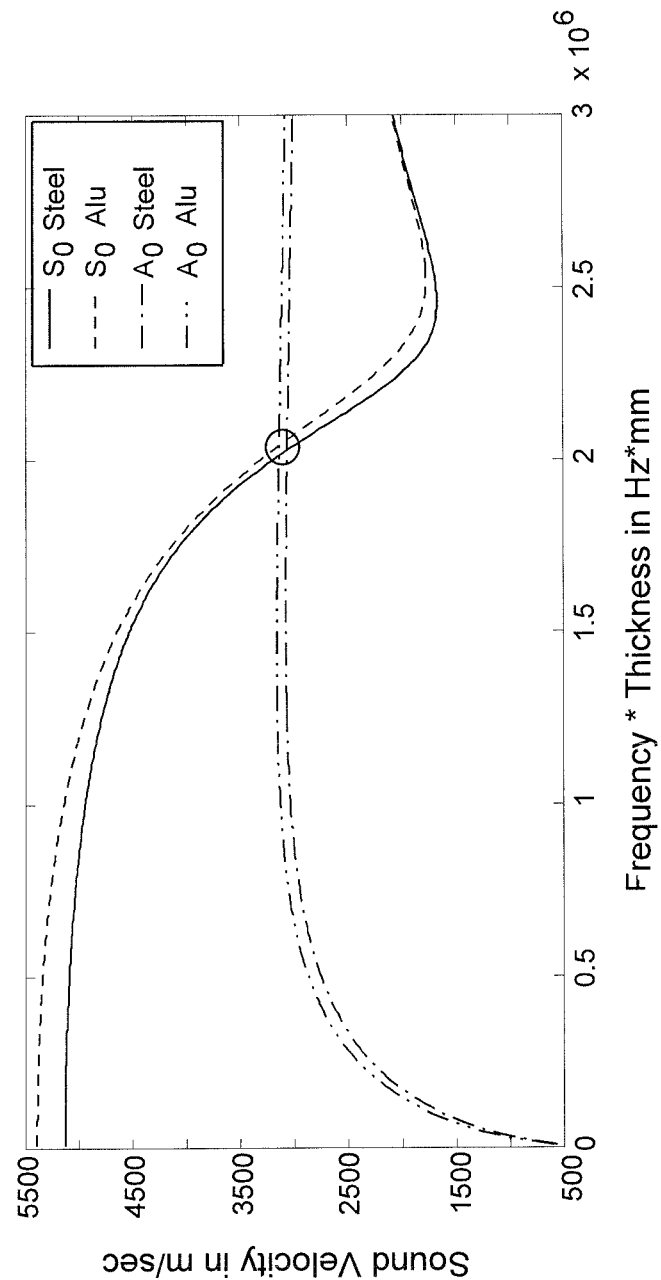

FIG. 5 a fourth embodiment for measuring the speed of sound in a gaseous medium above the liquid;

FIG. 6 a schematic behavior of the two zero-order modes of a Lamb wave;

FIG. 7 a dependency of speed of sound from wall thickness, wall material and signal frequency.

FIG. 2 shows a view from the top of a first embodiment for measuring the speed of sound in a liquid 22 contained in a vessel 21. A first acoustic transmitter 27 is mounted below the liquid surface and at the outside of vessel 21 for transmitting a first acoustic signal 29 into the liquid 22 to travel inside a first travelling plane towards a first receiver 25. The first travelling plane is in this case a circular plane lying horizontally and in parallel to the bottom of the vessel 21.

A first acoustic receiver 25 for receiving the first acoustic signal 29 is also mounted below the liquid surface. The first acoustic receiver 25 is in fact integrated in the same device as the first transmitter 27, and is arranged to receive the first acoustic signal 29 after it has been reflected by the wall of the vessel 21 which lies opposite to the wall where the transmitter 27 and receiver 25 are mounted at. Accordingly, the first transmitter 27 is arranged to emit the first acoustic signal 29 in a direction which is perpendicular to a first reflective surface of the wall of the vessel, so that the first acoustic signal 29 is reflected back towards its origin and thereby towards the first receiver 25.

The first transmitter 27 is further arranged to emit a second acoustic signal 20 in form of an acoustic wave into the wall of the vessel 21 to travel inside the wall of the vessel along a perimeter of the first travelling plane until it is received by the first acoustic receiver 25.

As described above, at least one electronic control and data processing unit 61, which is exemplary shown in FIG. 5 only, not only controls operation of the transmitter 27 and receiver 25 but is arranged in addition to obtain a first time of flight t1 of the first acoustic signal 29 and a second time of flight t2 of the second acoustic signal 20 by measuring the period of time between emission and reception of the respective signal;

obtain a speed of sound c_wall in the wall of the vessel 21 from a data memory wherein the speed of sound in the wall of the vessel 21 is assumed to be known and constant, i.e. it is saved in the data memory in advance as a parameter;

determine the perimeter P of the first travelling plane, i.e. the perimeter of the circle shown in FIG. 2, from the speed of sound in the vessel wall and from the second time of flight;

determine the length of the travelling path D of the first acoustic signal 29, which in this case is twice the length of the circle diameter, from the perimeter of the first travelling plane and from an information on the geometric shape of the first travelling plane; and determine the speed of sound c_liquid in the liquid 22 from the length of the travelling path of the first acoustic signal and from the first time of flight.

The information on the geometric shape of the first travelling plane is also stored in the data memory.

The perimeter P of the first travelling plane may be determined based on the general relationship P=t2*c_wall. The length of the travelling path D may be determined in case of a circle diameter based on the general relationship D=2*P/pi, and the speed of sound may be determined based on c_liquid=D/t1. In reality, additional physical effects have to be taken into account, such as delay times occurring in the electronics of transmitter and/or receiver.

Explained differently, FIG. 2 shows that for measuring the speed of sound in a liquid 22, two acoustical signals (29, 20) are generated, wherein one (29) travels through the medium to the opposite side of the vessel 21 and is reflected back, the other travels along the solid vessel wall, once around the vessel 21. The travel times of the two signals are measured. Since it was recognized that the sound velocity in the solid wall varies much less with the wall material and the temperature than in the liquid 22 inside the vessel, it is assumed to be known. The travel time in the vessel wall is used together with the assumed sound velocity to determine the vessel perimeter and thus the diameter. With the determined vessel diameter, the speed of sound can be calculated out of the travel time in the medium.

In FIG. 2, a first signal (29) is sent horizontally through the medium to the opposite side of the wall, where it is reflected back and received again at the sender (27, 25). A second signal (20) is generated as plate wave in the wall and travels through the wall around the circumference of the vessel (21). The second signal (20) will be also received again at the sender (27, 25). The travel times of both signals are measured. The time of flight of the first signal will be used as described above for the speed of sound measurement in the medium (22). The second signal is used for determining the perimeter length of the tank from which then the diameter and thus the traveled distance of the first signal (29) can be determined.

The length of the perimeter can be determined out of the time of flight of the second signal (20) analogue to equation (1), where again the propagation velocity has to be known, e.g. the speed of sound in the vessel wall. As can be seen from the speed of sound values given above for different wall materials, the variation for the speed of sound between different metals is much lower than for liquids or gases, especially for the shear wave velocity. Also, the variation with the temperature is by a factor of 10 lower compared to gases and liquids. Thus, the uncertainty in the perimeter measurement is lower than if the second signal (20) had been travelling in a liquid or gaseous medium. Additionally, only a small selection of materials is commonly used as wall material for process vessels and the used wall material is often known. Therefore, when the wall material class is known, the uncertainty will be even lower. Also, the temperature of the wall is easier to determine than the temperature of the medium, e.g. it can be measured by surface temperature sensors, and thus also the temperature dependency of the propagation velocity can be further compensated by a known temperature dependency of the wall material. Consequently, the uncertainty in the speed of sound of the medium which is used for the level measurement is reduced to the uncertainty of the speed of sound of the wall material.

In FIG. 3, a second embodiment is shown which differs from the embodiment of FIG. 2 in that the first acoustic signal 39 is not reflected back from the opposite vessel wall but measured with an additional transducer, to reduce the travel distance in case of a liquid 32 with a high damping factor. In the system of FIG. 3, the first transmitter 37 and the first receiver 35 are not integrated in the same device, but placed at different horizontal positions. The first transmitter 37 is arranged to emit the first acoustic signal 39 in an angular direction which is not perpendicular to a first reflective surface of the wall of the vessel, so that the first acoustic signal 39 travels straight towards the first receiver 35. Accordingly, the generated signals (39) for the speed of sound calibration do not need to travel over the full tank diameter/perimeter. In case that no difference is made between transmitter and receiver, but that transducers are used which have both emitting and receiving capability, an additional transducer may be used at a second point of the vessel's perimeter. In the same manner as shown in FIG. 3, the signals for the sound calibration (39) can be directed towards this second transducer and have to travel only a shorter distance. The second signals traveling through the vessel wall (30) would also be received by this second transducer and would also have to cover a shorter path only. This would be of advantage in case of high damping in either the liquid 32 or the wall of vessel 31 or both, or in case that an installation part in the vessel 31 would block a path straight through the middle of the vessel 31.

The third embodiment shown in FIG. 4 differs from the embodiment of FIG. 3 in that the first acoustic signal 49, which is to travel through the liquid 42, is not sent out straight to the receiving side, but under an angle. It is then reflected several times along the vessel wall. With this embodiment, problems with installations in the middle of the vessel 41 are avoided, i.e. blocking parts in the middle of the tank are no longer of concern. In the system of FIG. 4, the first transmitter 47 and the first receiver 45 are integrated in the same device and are mounted at the outside of the wall of vessel 41. The first transmitter 47 is arranged to emit the first acoustic signal 49 in an angular direction which is not perpendicular to a first reflective surface of the wall of the vessel, so that the first acoustic signal 39 is reflected more than once by the wall of the vessel 41 before it is received by the first receiver 45.

The fourth embodiment of FIG. 5 differs from the first embodiment of FIG. 2 in that a second transducer is mounted at a fixed distance from the first transducer in order to determine the speed of sound in the vessel wall, opposed to assuming that the speed of sound in the vessel wall is known and constant. The fixed distance may for example be ensured by mounting the two transducers together in one casing 53. In addition, the speed of sound is not determined in a liquid, but in the gaseous medium 52 which is present above the liquid in the vessel. This system may then provide the speed of sound in the gaseous medium to a level measurement device which is arranged at the top and inside the vessel and which measures the liquid level from an acoustic signal travelling through the gaseous medium.

In general, it is to be noted that all embodiments described here can be applied to either a liquid or a gaseous medium.

In FIG. 5, a first transmitter 57 and a first receiver 55 are integrated in one unit, and a second transmitter 67 and a second receiver 65 are integrated in another unit, both units being placed at different horizontal positions and with a fixed horizontal distance between each other inside the casing 53. The first transmitter 57 is arranged to emit a first acoustic signal 59 in a perpendicular direction to a first reflective surface of the wall of the vessel 51, so that the first acoustic signal 59 is reflected back to the first receiver 55. The second transmitter 67 is arranged to emit the second acoustic signal 50 into the wall of vessel 51 where it travels inside the vessel wall along the circular perimeter until it is received by the first receiver 55. The second time of flight determined for the second acoustic signal 50 corresponds to the perimeter minus the fixed distance between first transmitter-receiver 57, 55 and second transmitter-receiver 67, 65.

In addition, the first transmitter 57 is arranged to emit a third acoustic signal 60 into the wall of the vessel 51, and the second acoustic receiver is arranged to receive the third acoustic signal 60, The at least one electronic control and data processing unit 61 is arranged to determine a third time of flight of the third acoustic signal 60 by measuring the period of time between emission and reception of the third acoustic signal and to determine the speed of sound in the wall of the vessel from the predetermined distance between first transmitter 57 and second receiver 65 and from the third time of flight.

Alternatively, the embodiment of FIG. 5 could be varied by using the second acoustic receiver 65 only, but leaving out the second acoustic transmitter 67, i.e. by replacing the second transmitter-receiver 67, 65 by a pure receiver.

Accordingly, the first acoustic transmitter 57 would emit two acoustic signals 59, 50; the first acoustic receiver 55 would receive the reflection of the first acoustic signal 59; and the second acoustic receiver 65 would receive the second acoustic signal 50 after it has propagated the short direct distance between first transmitter 57 and second receiver 65 (in that way following the propagation path alike to the third acoustic signal 60) and then again after the second acoustic signal 50 continued travelling through the wall along the circumference of the vessel, where it is received again by the first receiver 55. The speed of sound and the perimeter are calculated out of these measured time of flights as described above.

In summary of the descriptions of the embodiments of FIGS. 2 to 5, it can be noted that the first acoustic signal is received by the first receiver either directly (FIG. 3) or as a reflection of it (FIGS. 2, 4, 5). Further, the vessels are all assumed to have a cylindrical shape at least in the area where the measurement of the speed of sound is performed. In FIGS. 2 to 5, the view is always shown from the top of the vessel 21, 31, 41, 51. Due to the cylindrical shape at the height of the speed of sound measurements, the walls of the vessels 21, 31, 41, 51 are all shown as circles. However, the solution proposed here is applicable to any other geometric form as long as this form allows for the travel length of the first acoustic signal to be obtained when knowing the perimeter of the plane across which the first acoustic signal propagates.

In the following, a further development of the embodiments of FIGS. 2 to 5 is described, where the first transmitter 27, 37, 47, 57 and/or the second transmitter 67 is arranged to emit the second or the third acoustic signal, respectively, as a lamb wave with a symmetrical zero-order mode S0 and an antisymmetric zero-order mode A0. The frequency behavior of these different lamb wave modes is used to take into account as a further vessel parameter the wall thickness, so as to determine the speed of sound in the wall of vessel 51 with a higher precision.

The acoustic waves which are emitted by the first or second transmitters 27, 37, 47, 57, 67 and which propagate in the vessel wall are commonly called plate or Lamb waves. They occur in different kinds of modes each having a different speed of sound and a different dependency of the speed of sound on the frequency f that also depends on the thickness d of the wall.

The dependency of the speed of sound or sound velocity of the two fundamental modes S0 and A0 from the frequency multiplied by the wall thickness is shown in FIG. 7 for the group velocity, where different graphs are depicted for the two wall materials aluminum and steel.

The two fundamental zero-order modes S0 and A0 are briefly explained in connection with FIG. 6. As can be seen, the symmetrical zero-order mode S0 moves inside a plate or wall having the thickness d in a symmetrical fashion with respect to the median plane of the plate positioned at half the thickness d/2. The symmetrical zero-order mode is also called the extensional mode because the wave stretches and compresses the plate in the wave motion direction. For the asymmetrical zero-order mode A0, the plate bends as its upper and lower surfaces move in the same direction. The asymmetrical zero-order mode is also called the flexural mode because most of the wave's movement takes place in a normal direction to the plate, and only little motion occurs in the direction parallel to the plate.

In FIG. 7, it is emphasized that the dependency of the Lamb wave's speed of sound from the frequency is coupled to its dependency from the wall thickness. This combined frequency/thickness dependency is described by the product out of frequency and thickness rd, which depicted in FIG. 7 on the x-axis of the diagram.

Assuming an invariable thickness, it can be seen from FIG. 7 that the sound velocity of the S0 mode is almost constant for low frequencies. The values between 5000 and 5500 m/s correspond to the above given sound velocities of a longitudinal wave in an aluminum or steel bulk material, respectively. For higher frequencies, the speed of sound of the S0 mode decreases.

The sound velocity of the A0 mode increases with the frequency up to the value of about 3000 m/s, given above as the shear velocity in an aluminum or steel bulk material. At higher frequencies, the speed of sound of the A0 mode remains nearly constant. At higher frequencies, also the difference between the sound velocity of steel and aluminum for the A0 mode is comparatively low. It would thus be of advantage to use for the second and/or third acoustic signal 20, 30, 40, 50, 60 a frequency in this higher frequency range.

The symmetric S0 mode also shows for higher frequencies, when the speed of sound decreases, a quite similar behavior for the different materials, resulting in the sound velocity for the different materials to be quite similar in the higher frequency*thickness range. This is another reason why this frequency*thickness range would be interesting to be used for further decreasing the uncertainty in the sound velocity.

Because the exact wall thickness is often not known a priori and because the sound velocity of the different modes depends on the frequency*thickness product, the graph shown in FIG. 7 can be made use of. To do that it needs to be known in which part or at which point in the c(f*d) curve of FIG. 7 the correct sound velocity in the wall can be obtained. For simple measurements as described above, a low frequency can be chosen in case of a measurement with the symmetric S0 mode, or a high frequency can be chosen in case of a measurement with the asymmetric A0 mode, where the respective frequency is chosen in such a way that for all values of wall thickness which are to be expected the resulting product of frequency and wall thickness would still result in a sound velocity belonging to the respective constant range in sound velocity.

To further reduce the variance in the speed of sound of the vessel wall material, it is of advantage to use a fixed frequency*thickness value every time a measurement is performed. It has been recognized that an easily detectable frequency*thickness value would be the crossing of the speed of sound values for the two different modes, as indicated in FIG. 7 by the circle. This crossing point would help to stay at a fixed frequency*thickness value in case of an unknown or changing wall thickness. The crossing could be detected by exciting in the transmitters 27, 37, 47, 57, 67 pulses of both propagation modes S0 and A0 with varying frequencies. Varying the frequency means that the frequency may be linearly increased or decreased between taking measurements, or that it is changed according to a predetermined pattern or even at random. When the pulses of the two modes S0 and A0 arrive at the respective receiver 25, 35, 45, 55, 65 at the same time, the crossing point of the two modes is reached. But also other frequency*thickness values can be detected by comparing the frequency behavior of the two modes, as e.g. by comparing the relation of the propagation or speed velocities of the two modes by each other as c_S0/c_A0. For a given frequency*thickness value this relation would be constant, and by varying the frequency until the relation of the time of flight for the two modes will be inversely equal to this relation of the propagation velocity t_A0/t_S0=c_S0/c_A0, a fixed frequency*thickness value can be obtained.

But also the use of higher order modes is possible to determine specific frequency*thickness values or to get ranges with low sound velocity variances of the wall material.

Additionally, by determining the frequency at which this fixed frequency*thickness value is obtained, the wall thickness may be calculated out of it with the thus known frequency.

A further improvement to reduce the uncertainty in the sound velocity of the wall material is achieved with the system shown in FIG. 5, where the sound velocity in the wall is measured by adding a second receiver 65. The second receiver 65 is placed outside on the vessel wall at a predefined distance to the first transmitter 55. The first transmitter 57 and the first receiver 55 are advantageously combined in a first transducer, and the second transmitter 67 and the second receiver 65 are advantageously combined in a second transducer. With a time of flight measurement between the two transducers, the speed of sound can be determined analogous to equation (2).

The position of the second transducer would be chosen such that an easy measurement of the distance is possible in advance. As explained previously, the two transducers can even be included in the same casing 53 to automatically provide a known distance without the need of an additional user input.

In the case of FIG. 4, where the first signal 49 is sent out under an angle and is reflected several times along the perimeter until it reaches the first receiver 45 or a second receiver along the path (not shown), the signal travels all the time close to the wall so as to be unaffected by installations in the middle of the vessel 41. Such a path could be generated by using Lamb waves in a similar way as used for the perimeter/diameter measurement (second signals 20, 30, 40, 50), since certain modes of Lamb waves may radiate acoustic waves from the wall into the liquid, depending on the product frequency*thickness. This kind of Lamb waves is also called leaky Lamb waves. Leaky Lamb waves occur for example in the case of the A0 mode at a wide range of frequency*thickness values, when the wall in which the A0 mode propagates is next to a liquid. The direction of the radiated beam is not perpendicular to the wall but under an angle which depends on the sound velocity of the Lamb wave and the sound velocity in the liquid. Thus, by generating Lamb waves with different exciting modes and frequencies the signals for measuring the perimeter/diameter as well as for the sound velocity calibration can be generated.

In the presence of a liquid, the Lamb waves in the wall can be dampened depending on the mode and its frequency*thickness value. Therefore, it is of advantage to perform the perimeter/diameter measurement with the second signals 20, 30, 40, 50 at an empty tank. The perimeter/diameter measurement needs only to be done once after the installation and can then be used for the further measurements of the speed of sound in the liquid or gaseous medium and of the liquid level.

The invention claimed is:

1. System for measuring a speed of sound in a liquid contained in a vessel or in a gaseous medium contained in the same vessel above the surface of the liquid, the system comprising
a first acoustic transmitter mounted on one side of the liquid surface for transmitting a first acoustic signal into the liquid or into the gaseous medium to travel inside a first travelling plane,
a first acoustic receiver mounted on the same side of the liquid surface as the first transmitter for receiving the first acoustic signal,
at least one electronic control and data processing unit for controlling operation of the transmitter and of the receiver and for determining the speed of sound from a time of flight of the first acoustic signal, wherein
the first transmitter or a second transmitter is further arranged to emit a second acoustic signal in form of an acoustic wave into the wall of the vessel to travel inside the wall of the vessel along a perimeter of the first travelling plane until it is received by the first acoustic receiver or by a second acoustic receiver which is placed at a predetermined distance from the first or second transmitter, respectively;
the at least one electronic control and data processing unit is arranged to
obtain a first time of flight of the first acoustic signal and a second time of flight of the second acoustic signal by measuring the period of time between emission and reception of the respective signal;
obtain a speed of sound in the vessel wall from a data memory, wherein the speed of sound in the vessel wall may be a predetermined value or a measured value;
determine the perimeter of the first travelling plane from the speed of sound in the vessel wall and from the second time of flight,
determine the length of the travelling path of the first acoustic signal from the perimeter of the first travelling plane and from an information on the geometric shape of the first travelling plane obtained from the data memory,
determine the speed of sound in the liquid or in the gaseous medium from the length of the travelling path of the first acoustic signal and from the first time of flight.

2. System according to claim 1, wherein the first transmitter and the first receiver are integrated in the same device.

3. System according to claim 2, wherein the first transmitter is arranged to emit the first acoustic signal in an angular direction which is not perpendicular to a first reflective surface of the wall of the vessel.

4. System according to claim 2, wherein
the first transmitter is arranged to emit a third acoustic signal into the wall of the vessel,
a second acoustic receiver is mounted to the outside of the wall of the vessel at a predetermined distance to the first transmitter and is arranged to receive the third acoustic signal, and
the at least one electronic control and data processing unit is arranged to determine a third time of flight of the third acoustic signal by measuring the period of time between emission and reception of the third acoustic signal and to determine the speed of sound in the wall of the vessel from the predetermined distance between first transmitter and second receiver and from the third time of flight.

5. System according to claim 2, wherein the first transmitter and/or the second transmitter is arranged to emit the second acoustic signal as a Lamb wave with a symmetric zero-order mode and an asymmetric zero-order mode.

6. System according to claim 2, wherein the first or the second transmitter, the first receiver and the at least one electronic control and data processing unit are arranged to perform the determination of the perimeter of the first travelling plane either when the vessel is empty or at a height of the wall of the vessel which is not in contact with any liquid.

7. System according to claim 2, wherein the first transmitter is arranged to emit the first acoustic signal in a direction which is perpendicular to a first reflective surface of the wall of the vessel.

8. System according to claim 7, wherein the first or the second transmitter, the first receiver and the at least one electronic control and data processing unit are arranged to perform the determination of the perimeter of the first travelling plane either when the vessel is empty or at a height of the wall of the vessel which is not in contact with any liquid.

9. System according to claim 1, wherein the first transmitter and the first receiver are placed at differing horizontal and/or vertical positions.

10. System according to claim 9, wherein the first transmitter is arranged to emit the first acoustic signal in an angular direction which is not perpendicular to a first reflective surface of the wall of the vessel.

11. System according to claim 1, wherein
the first transmitter is arranged to emit a third acoustic signal into the wall of the vessel,
a second acoustic receiver is mounted to the outside of the wall of the vessel at a predetermined distance to the first transmitter and is arranged to receive the third acoustic signal, and
the at least one electronic control and data processing unit is arranged to determine a third time of flight of the third acoustic signal by measuring the period of time between emission and reception of the third acoustic signal and to determine the speed of sound in the wall of the vessel from the predetermined distance between first transmitter and second receiver and from the third time of flight.

12. System according to claim 1, wherein the first transmitter and/or the second transmitter is arranged to emit the second acoustic signal as a Lamb wave with a symmetric zero-order mode and an asymmetric zero-order mode.

13. System according to claim 12, wherein in case that the thickness of the vessel wall is known, the at least one electronic control and data processing unit is arranged to obtain the speed of sound in the vessel wall from a graph of speed of sound in the wall material versus the mathematical product of wave frequency and wall thickness and to store it in the data memory, by choosing as wave frequency for the symmetric or the asymmetric zero-order mode a frequency which in the graph belongs to a range of approximately constant speed of sound in the wall material, and wherein the at least one electronic control and data processing unit is arranged to control the first transmitter and/or the second transmitter to emit the symmetric or the asymmetric zero-order mode at the respectively chosen wave frequency.

14. System according to claim 13, wherein the first transmitter and/or the second transmitter are arranged to emit the symmetric zero-order mode and the asymmetric zero-order mode with varying frequency and wherein the at least one electronic control and data processing unit is arranged to detect the specific frequency at which the symmetric zero-order mode and the asymmetric zero-order mode are received simultaneously by the first receiver, and to store in the data memory a value for the speed of sound in the wall of the vessel which corresponds to the overlapping of a graph of speed of sound versus the mathematical product of wave frequency and wall thickness for the symmetric zero-order mode with the same type of graph for the asymmetric zero-order mode.

15. System according to claim 12, wherein in case that the thickness of the vessel wall is unknown, the at least one electronic control and data processing unit is arranged to obtain the speed of sound in the vessel wall from a graph of speed of sound in the wall material versus the mathematical product of wave frequency and wall thickness and to store it in the data memory, by choosing as wave frequency for the symmetric or the asymmetric zero-order mode a frequency which for all to be expected values of wall thickness would result in a product of wave frequency and wall thickness which in the graph belongs to a range of approximately constant speed of sound in the wall material, and wherein the at least one electronic control and data processing unit is arranged to control the first transmitter and/or the second transmitter to emit the symmetric or the asymmetric zero-order mode at the respectively chosen wave frequency.

16. System according to claim 15, wherein the first transmitter and/or the second transmitter are arranged to emit the symmetric zero-order mode and the asymmetric zero-order mode with varying frequency and wherein the at least one electronic control and data processing unit is arranged to detect the specific frequency at which the symmetric zero-order mode and the asymmetric zero-order mode are received simultaneously by the first receiver, and to store in the data memory a value for the speed of sound in the wall of the vessel which corresponds to the overlapping of a graph of speed of sound versus the mathematical product of wave frequency and wall thickness for the symmetric zero-order mode with the same type of graph for the asymmetric zero-order mode.

17. System according to claim 12, wherein the first transmitter and/or the second transmitter are arranged to emit the symmetric zero-order mode and the asymmetric zero-order mode with varying frequency and wherein the at least one electronic control and data processing unit is arranged to detect the specific frequency at which the symmetric zero-order mode and the asymmetric zero-order mode are received simultaneously by the first receiver, and to store in the data memory a value for the speed of sound in the wall of the vessel which corresponds to the overlapping of a graph of speed of sound versus the mathematical product of wave frequency and wall thickness for the symmetric zero-order mode with the same type of graph for the asymmetric zero-order mode.

18. System according to claim 1, wherein the first or the second transmitter, the first receiver and the at least one electronic control and data processing unit are arranged to perform the determination of the perimeter of the first travelling plane either when the vessel is empty or at a height of the wall of the vessel which is not in contact with any liquid.

19. Method for measuring a speed of sound in a liquid contained in a vessel or in a gaseous medium contained in the same vessel above the surface of the liquid, the method comprising the steps
transmitting a first acoustic signal into the liquid or into the gaseous medium by a first acoustic transmitter mounted on one side of the liquid surface, wherein the first acoustic signal is emitted to travel inside a first travelling plane,
receiving the first acoustic signal by a first acoustic receiver mounted on the same side of the liquid surface as the first transmitter,
controlling operation of the transmitter and of the receiver and determining the speed of sound from a time of flight of the first acoustic signal by at least one electronic control and data processing unit, wherein emitting a second acoustic signal in form of an acoustic wave into the wall of the vessel by the first transmitter or by a second transmitter, wherein the second acoustic signal is emitted to travel inside the wall of the vessel along a perimeter of the first travelling plane until it is received by the first acoustic receiver;

obtaining a first time of flight of the first acoustic signal and a second time of flight of the second acoustic signal by measuring the period of time between emission and reception of the respective signal;

obtaining a speed of sound in the vessel wall from a data memory, wherein the speed of sound in the vessel wall may be a predetermined value or a measured value;

determining the perimeter of the first travelling plane from the speed of sound in the vessel wall and from the second time of flight, determining the length of the travelling path of the first acoustic signal from the perimeter of the first travelling plane and from an information on the geometric shape of the first travelling plane obtained from the data memory, determining the speed of sound in the liquid or in the gaseous medium from the length of the travelling path of the first acoustic signal and from the first time of flight.

20. Method according to claim 19, wherein the speed of sound in the liquid or in the gaseous medium is used as an input value for measuring the level of the liquid in the vessel.

* * * * *